United States Patent
Kano

(10) Patent No.: US 12,217,847 B2
(45) Date of Patent: Feb. 4, 2025

(54) MEDICAL TREATMENT SUPPORT APPARATUS

(71) Applicant: CANON MEDICAL SYSTEMS CORPORATION, Tochigi (JP)

(72) Inventor: Yusuke Kano, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 572 days.

(21) Appl. No.: 17/454,083

(22) Filed: Nov. 9, 2021

(65) Prior Publication Data

US 2022/0148700 A1   May 12, 2022

(30) Foreign Application Priority Data

Nov. 9, 2020   (JP) .................................. 2020-186313
Nov. 5, 2021   (JP) .................................. 2021-181210

(51) Int. Cl.
*G16H 10/60*   (2018.01)
*G16H 20/40*   (2018.01)

(52) U.S. Cl.
CPC ............. *G16H 20/40* (2018.01); *G16H 10/60* (2018.01)

(58) Field of Classification Search
CPC ........ G16H 20/40; G16H 10/60; G16H 20/10; G16H 20/00
See application file for complete search history.

(56) References Cited

U.S. PATENT DOCUMENTS

| | | | |
|---|---|---|---|
| 2007/0192132 A1* | 8/2007 | Thesman ............... | G16H 10/60 705/2 |
| 2009/0259488 A1* | 10/2009 | Gounares ............... | G16H 70/20 705/7.42 |
| 2010/0191071 A1* | 7/2010 | Anderson .............. | G16H 50/50 703/11 |
| 2015/0234992 A1 | 8/2015 | Dries et al. | |
| 2017/0323064 A1* | 11/2017 | Bates ..................... | G16H 50/20 |

FOREIGN PATENT DOCUMENTS

JP   2015-534161 A   11/2015

* cited by examiner

*Primary Examiner* — Charles Cai
(74) *Attorney, Agent, or Firm* — Oblon, McClelland, Maier & Neustadt, L.L.P.

(57) ABSTRACT

A medical treatment support apparatus according to one embodiment includes processing circuitry. About a treatment plan for a disease of a patient, the processing circuitry predicts a decision of subjects who are the patient or people who are involved with the patient and a decision of a doctor who determines the treatment plan for the subject. The processing circuitry presents information based on a result of the prediction to the doctor and at least one of the subjects.

15 Claims, 10 Drawing Sheets

FIG.3A

| DOCTOR (MDT) | |
|---|---|
| SAVR | $p_1^D = 0.2$ |
| TAVI | $p_2^D = 0.2$ |
| MEDICATION | $p_3^D = 0.6$ |
| NO TREATMENT | $p_4^D = 0.1$ |

FIG.3B

| PATIENT | |
|---|---|
| SAVR | $p_1^P = 0.3$ |
| TAVI | $p_2^P = 0.5$ |
| MEDICATION | $p_3^P = 0.2$ |
| NO TREATMENT | $p_4^P = 0.1$ |

FIG.4

| PATIENT ID | PATIENT NAME | DECISION MAKING | | COLLISION RISK |
| --- | --- | --- | --- | --- |
| | | PATIENT | MDT | |
| 000001 | SHINZO ICHIRO | TAVI | TAVI | |
| 000002 | SHINZO JIRO | SAVR | TAVI | ! |
| 000003 | SHINZO SABURO | SAVR | SAVR | |
| 000004 | SHINZO SHIRO | MEDICATION | TAVI | ⚠ |
| 000005 | SHINZO GORO | SAVR | SAVR | |
| 000006 | SHINZO ROKURO | SAVR | SAVR | ⚠ |
| ... | | | | |

FIG.6

| PATIENT ID | PATIENT NAME | DECISION MAKING | | | COLLISION RISK | RECOMMENDED ACTION | |
|---|---|---|---|---|---|---|---|
| | | PATIENT | MDT | | | | |
| 000001 | SHINZO ICHIRO | TAVI | TAVI | TAVI | | | AGREEMENT |
| 000002 | SHINZO JIRO | SAVR | TAVI | | ! | MDT | EXAMINE ALTERNATIVE PLAN |
| 000003 | SHINZO SABURO | SAVR | TAVI | | | DOCTOR IN CHARGE | UNDERSTAND DECISION |
| 000004 | SHINZO SHIRO | MEDICATION | SAVR | TAVI | ⚠ | DOCTOR IN CHARGE | FORM AGREEMENT |
| 000005 | SHINZO GORO | SAVR | TAVI | SAVR | | MDT | DETERMINE PLAN |
| 000006 | SHINZO ROKURO | MEDICATION | SAVR | SAVR | ⚠ | DOCTOR IN CHARGE | EXPLAIN ADDITIONALLY |
| ... | | | | | | | |

FIG.7

| | SAVR (SURGERY) | TAVI (CATHETER-IZATION) | MEDICATION (INTERNAL TREATMENT) | NO TREATMENT (FOLLOW-UP) |
|---|---|---|---|---|
| DOCTOR (MDT) | ○ | ○ | × | × |
| PATIENT | × | ○ | ○ | ○ |

FIG.8

| | SAVR (SURGERY) | TAVI (CATHETER-IZATION) | MEDICATION (INTERNAL TREATMENT) | NO TREATMENT (FOLLOW-UP) |
|---|---|---|---|---|
| DOCTOR (MDT) | $p_1^D = 0.4$ | $p_2^D = 0.4$ | $p_3^D = 0.1$ | $p_4^D = 0.1$ |
| PATIENT | $p_1^P = 0.1$ | $p_2^P = 0.6$ | $p_3^P = 0.2$ | $p_4^P = 0.1$ |

FIG.9

| | SAVR (SURGERY) | TAVI (CATHETER- IZATION) | MEDICATION (INTERNAL TREATMENT) | NO TREATMENT (FOLLOW-UP) |
|---|---|---|---|---|
| DOCTOR (MDT) | $p_1^D = 0.4$<br>$q_1^D = 0.7$ | $p_2^D = 0.4$<br>$q_2^D = 0.8$ | $p_3^D = 0.1$<br>$q_3^D = 0.4$ | $p_4^D = 0.1$<br>$q_4^D = 0.2$ |
| PATIENT | $p_{1_D}^P = 0.1$<br>$q_{1_D}^P = 0.3$ | $p_{2_D}^P = 0.6$<br>$q_{2_D}^P = 0.9$ | $p_{3_D}^P = 0.2$<br>$q_{3_D}^P = 0.6$ | $p_{4_D}^P = 0.1$<br>$q_{4_D}^P = 0.1$ |

FIG.10

| | SAVR (SURGERY) | TAVI (CATHETER- IZATION) | MEDICATION (INTERNAL TREATMENT) | NO TREATMENT (FOLLOW-UP) |
|---|---|---|---|---|
| DOCTOR (MDT) | $p_1^D = 0.5$ | $p_2^D = 0.3$ | $p_3^D = 0.1$ | $p_4^D = 0.1$ |
| PATIENT | $p_1^P = 0.3$ | $p_2^P = 0.1$ | $p_3^P = 0.5$ | $p_4^P = 0.1$ |

FIG.11

| PATIENT ID | PATIENT NAME | DECISION MAKING | | | COLLISION RISK | RECOMMENDED ACTION | |
|---|---|---|---|---|---|---|---|
| | | PATIENT | | MDT | | | |
| 000001 | SHINZO ICHIRO | TAVI | TAVI | TAVI | | | AGREEMENT |
| 000002 | SHINZO JIRO | SAVR | TAVI | TAVI | ⊙ | MDT | EXAMINE ALTERNATIVE PLANS (2) |
| 000003 | SHINZO SABURO | SAVR | SAVR | SAVR | | DOCTOR IN CHARGE | UNDERSTAND DECISION |
| 000004 | SHINZO SHIRO | MEDICATION | TAVI | TAVI | ⚠ | DOCTOR IN CHARGE | FORM AGREEMENT |
| 000005 | SHINZO GORO | SAVR | SAVR | SAVR | | MDT | DETERMINE PLAN |
| 000006 | SHINZO ROKURO | MEDICATION | SAVR | SAVR | ⚠ | MDT | DETERMINE PLAN |
| ... | | | | | | | |

FIG.12A

PROBABILITIES OF DOCTOR'S (MDT) CHOICE

| BEFORE PRESENTATION | | AFTER PRESENTATION | TREAT-MENT A | TREAT-MENT B | TREAT-MENT C |
|---|---|---|---|---|---|
| TREAT-MENT A | 0.1 | TREAT-MENT A | 0.6 | 0.1 | 0.3 |
| TREAT-MENT B | 0.2 | TREAT-MENT B | 0.2 | 0.2 | 0.6 |
| TREAT-MENT C | 0.7 | TREAT-MENT C | 0.2 | 0.0 | 0.8 |

$p^D(i)$ $\qquad$ $p_i^D(j)$

FIG.12B

PROBABILITIES OF PATIENT'S CHOICE

| BEFORE PRESENTATION | | AFTER PRESENTATION | TREAT-MENT A | TREAT-MENT B | TREAT-MENT C |
|---|---|---|---|---|---|
| TREAT-MENT A | 0.3 | TREAT-MENT A | 0.2 | 0.6 | 0.2 |
| TREAT-MENT B | 0.6 | TREAT-MENT B | 0.2 | 0.8 | 0.0 |
| TREAT-MENT C | 0.1 | TREAT-MENT C | 0.4 | 0.6 | 0.0 |

$p^P(i)$ $\qquad$ $p_i^P(j)$

MEDICAL TREATMENT SUPPORT APPARATUS

CROSS-REFERENCE TO RELATED APPLICATIONS

This application is based upon and claims the benefit of priority from Japanese Patent Application No. 2020-186313, filed on Nov. 9, 2020 and Japanese Patent Application No. 2021-181210, filed on Nov. 5, 2021; the entire contents of which are incorporated herein by reference.

FIELD

Embodiments described herein relate to a medical treatment support apparatus.

BACKGROUND

As the treatment becomes more advanced, the decision making by a multidisciplinary team (MDT) is recommended more frequently. For example, in a case of patients with a valvular disease in the heart, more patients have come to rely on the MDT to determine the treatment plan for the disease as to whether they have surgery or catheterization as advanced treatment. On the other hand, when deciding on a treatment plan, shared decision making, which is the decision making performed in consideration of the patient's decision, has become more important. The patient's decision is determined by the conversation between the patient and the patient's doctor, for example.

However, not all the members of the MDT meet the patient in person and the patient's decision and the MDT's decision are not always the same. In such a case, the treatment plan needs to be reconsidered.

BRIEF DESCRIPTION OF THE DRAWINGS

FIG. 3A is a diagram for describing the process by the medical treatment support apparatus according to the first embodiment;

FIG. 3B is a diagram for describing the process by the medical treatment support apparatus according to the first embodiment;

FIG. 4 is a diagram illustrating one example of a screen presented to an MDT and a patient's doctor;

FIG. 6 is a diagram illustrating one example of the screen presented to the MDT and the patient's doctor;

FIG. 7 is a diagram for describing a process by the medical treatment support apparatus according to a second embodiment;

FIG. 8 is a diagram for describing the process by the medical treatment support apparatus according to the second embodiment;

FIG. 9 is a diagram for describing the process by the medical treatment support apparatus according to the second embodiment;

FIG. 10 is a diagram for describing a process by the medical treatment support apparatus according to a third embodiment;

FIG. 11 is a diagram illustrating one example of the screen presented to the MDT and the patient's doctor in a case where two processes to be performed by the MDT are chosen;

FIG. 12A is a diagram for describing a process by the medical treatment support apparatus according to a fourth embodiment;

FIG. 12B is a diagram for describing the process by the medical treatment support apparatus according to the fourth embodiment;

DETAILED DESCRIPTION

A medical treatment support apparatus according to one embodiment includes processing circuitry. About a treatment plan for a disease of a patient, the processing circuitry predicts a decision of subjects who are the patient or people who are involved with the patient and a decision of a doctor who determines the treatment plan for the subjects. The processing circuitry presents the information based on the result of the prediction to the doctor and at least one of the subjects.

Embodiments of the medical treatment support apparatus are hereinafter described in detail with reference to the attached drawings. A medical treatment support system including the medical treatment support apparatus is hereinafter described as one example.

First Embodiment

Figure 1:
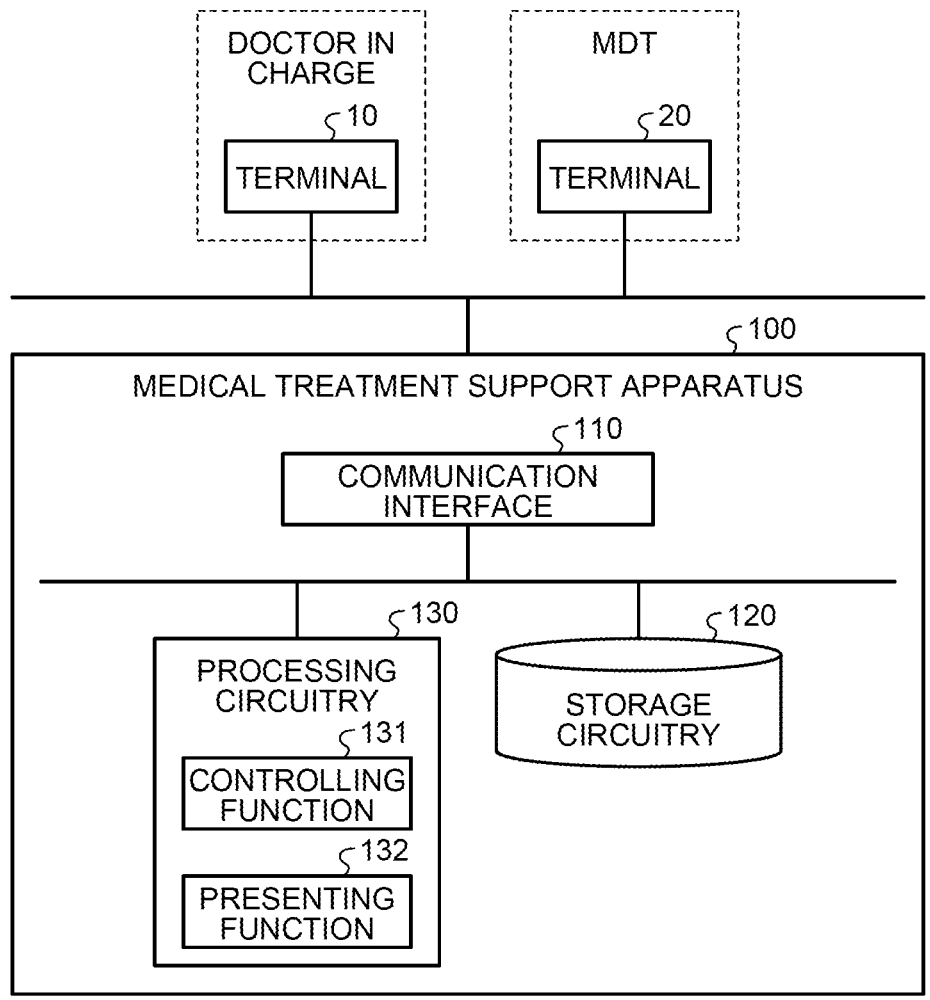
FIG. 1 is a diagram illustrating one example of a structure of a medical treatment support system including a medical treatment support apparatus according to a first embodiment.

FIG. 1 is a diagram illustrating one example of a structure of a medical treatment support system 1 including a medical treatment support apparatus 100 according to a first embodiment. The medical treatment support system illustrated in FIG. 1 includes a medical treatment support apparatus 100 and terminals 10 and 20. The medical treatment support apparatus 100 performs communication with the terminals 10 and 20.

For example, the terminals 10 and 20 include a personal computer (PC), a tablet type PC, a personal digital assistant (PDA), a mobile terminal, and the like.

The terminal 10 is provided in the patient's regular hospital and used by the patient's doctor.

The terminal 20 is used by a multidisciplinary team (hereinafter referred to as MDT) who belongs to the patient's regular hospital or another advanced and specialized hospital. Note that the MDT is one example of the first doctor, and the patient's doctor is one example of the second doctor.

The medical treatment support apparatus 100 includes a communication interface 110, storage circuitry 120, and processing circuitry 130. The communication interface 110 is connected to the processing circuitry 130, and controls the communication and the transmission of various kinds of data between the medical treatment support apparatus 100 and the terminals 10 and 20.

The storage circuitry 120 is connected to the processing circuitry 130, and stores various kinds of data therein. For example, the storage circuitry 120 is achieved by a semiconductor memory element such as a RAM or a flash memory, a hard disk, an optical disk, or the like. Note that the storage circuitry 120 is one example of a means that achieves a storage unit. Moreover, the storage circuitry 120 is not necessarily incorporated in the medical treatment support apparatus 100 as long as the medical treatment support apparatus 100 can be accessed on a network.

The storage circuitry 120 stores a plurality of pieces of patient information from electronic medical records created for each of a plurality of patients, for example. Each piece of patient information includes basic information and medical treatment data of the patient. The basic information includes identification information that identifies the patient, name, birthday, sex, blood type, height, weight, and the like. The medical treatment data includes information about numerals (measurement values), the medical records, and the like and information expressing the recording date. Examples of the medical treatment data include prescription data, nurse's record data, and the like. The prescription data is the medical treatment data about the prescription. The nurse's record data is the medical treatment data about the nurse's record.

Note that the data and the information stored in the storage circuitry 120 and used in the embodiment are described below.

The processing circuitry 130 controls the components of the medical treatment support apparatus 100. For example, the processing circuitry 130 performs a controlling function 131 and a presenting function 132 as illustrated in FIG. 1. Here, for example, the processing functions performed by the controlling function 131 and the presenting function 132, which are the components of the processing circuitry 130, are recorded in the storage circuitry 120 as computer-executable computer programs. The processing circuitry 130 is a processor that reads out each computer program from the storage circuitry 120 and executes the computer program, thereby achieving the function corresponding to the computer program. In other words, the processing circuitry 130 that has read out the computer program has the corresponding function in the processing circuitry 130 illustrated in FIG. 1.

The medical treatment support apparatus 100 has a display application (computer program) implemented therein, and the display application can be read out by the terminals 10 and 20. For example, users of the terminals 10 and 20 can cause displays of the terminals to display the display data transmitted from the medical treatment support apparatus 100 using the display application read out by the terminals. Note the controlling function 131 is one example of a prediction unit. The presenting function 132 is one example of a presentation unit.

The term "processor" used in the above description refers to a circuit such as a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). If the processor is a CPU, for example, the processor can achieve the function by reading out and executing the computer program saved in the storage circuitry 120. On the other hand, if the processor is an ASIC, for example, the computer program is not saved in the storage circuitry 120 but the computer program is incorporated directly in the circuitry of the processor. Note that each processor in the present embodiment is not limited to a structure formed as a single circuit for each processor, and a plurality of independent circuits may be combined and formed as one processor to achieve the function. Furthermore, a plurality of components illustrated in FIG. 1 may be integrated into one processor to achieve the function.

The overall structure of the medical treatment support system including the medical treatment support apparatus 100 according to the first embodiment is described above. With this structure, the medical treatment support apparatus 100 avoids the reconsideration of the treatment plan while reducing the burden in the decision making.

As the treatment becomes more advanced, the decision making by the MDT is recommended more frequently. For example, in the case of the patients with the valvular disease in the heart, more patients have come to rely on MDT to determine the treatment plan for the disease as to whether they have the surgery or the catheterization as the advanced treatment.

On the other hand, when the treatment plan is determined, shared decision making, which is the decision making performed in consideration of the patient's decision, has become more important. The patient's decision is determined by the conversation between the patient and the patient's doctor, for example.

However, not all the members of the MDT meet the patient in person and the patient's decision and the MDT's decision are not always the same. Therefore, in the case where the patient's decision and the MDT's decision do not coincide, the treatment plan needs to be reconsidered. For example, it is assumed that, as a result of the conversation between the patient and the patient's doctor, the patient wants to have the surgery. However, after the subsequent discussion in the MDT, the medication is chosen over the surgery. In this case, the treatment plan is reconsidered.

Reconsidering the treatment plan burdens the patient, the patient's doctor, and the MDT for the decision making. For example, if the patient disagrees after the patient's doctor explains the treatment plan that the MDT has determined, the doctor needs to have another conversation with the patient about the treatment plan and in this case, the patient is burdened. After this additional conversion, it is assumed that the patient wants to have the catheterization. In this case, another discussion is necessary in the MDT, and the MDT is also burdened. In view of this, it is necessary to avoid the reconsideration about the treatment plan so that neither the patient nor the MDT is burdened for the decision making.

In view of this, the medical treatment support apparatus 100 according to the first embodiment performs the following process. First, in the medical treatment support apparatus 100 according to the first embodiment, regarding the treatment plan for the disease of the patient, the controlling function 131 predicts the decision of the patient and the decision of the MDT who determines the treatment plan for the patient. The presenting function 132 presents the information based on the result of the prediction by the controlling function 131 to the MDT and the doctor in charge of confirming the patient's decision.

Figure 2:
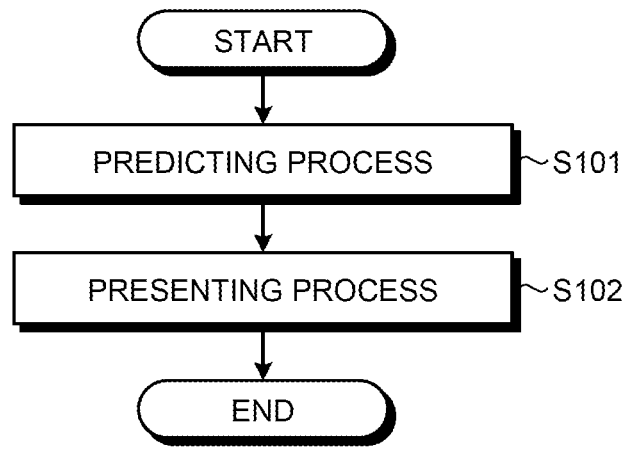
FIG. 2 is a flowchart illustrating a procedure of a process by the medical treatment support apparatus according to the first embodiment.

The respective functions of the controlling function 131 and the presenting function 132 are hereinafter described with reference to FIG. 2 to FIG. 6. FIG. 2 is a flowchart illustrating a procedure of the process by the medical treatment support apparatus 100 according to the first embodiment.

Step S101 in FIG. 2 is a step where the processing circuitry 130 calls a computer program corresponding to the controlling function 131 from the storage circuitry 120 and executes the computer program. At step S101, the controlling function 131 performs a predicting process. Specifically, regarding a treatment plan for a disease of a patient P, the controlling function 131 predicts the decision of the patient P and the decision of the MDT who determines the treatment plan for the patient P.

Here, in the present embodiment, for example, the storage circuitry 120 stores therein, in addition to the pieces of patient information described above, first information about the decision making by the patient P or by a patient group G with the same attribute as the patient P. Specifically, the first information is about the tendency of the treatment plan desired by the patient P and, for example, in the case where the disease is the valvular disease, the information expressing whether the patient group G wanted to have the treatment such as surgery, catheterization, or medication, or did not want the treatment, for example. Such first information is acquired by extracting the patient P's past information or patient history information of at least one patient with the same attribute as the patient P from among the patient history information in which decision making information about the decision making performed by various patients in the past is associated with the disease information of the patients, and the attribute information such as age, age group, sex, family structure, and residential area. Note that the attribute to be used beside the disease information among various kinds of attribute information when the patient group G is determined is the parameter that can be set by the user of the medical treatment support apparatus 100.

Furthermore, the storage circuitry 120 stores therein second information about the decision making performed by the MDT or by a doctor group with the same attribute as the MDT. Specifically, the second information is about the tendency of the treatment plan suggested by a medical specialist, for example by the MDT, and in the case where the disease of the patient P is the valvular disease, the information expressing whether the medical specialist suggested the treatment such as surgery, catheterization, or medication, or suggested that the treatment was not conducted. Note that in the case where there is not enough information on the past decision making about the MDT in charge of the patient P, the second information is acquired from the information about the decision making performed by another MDT on the same disease as the disease of the patient P in the hospital to which the MDT belongs.

The controlling function 131 predicts the patient P's decision and the MDT's decision on the basis of the first information and the second information stored in the storage circuitry 120 about the treatment plan for the disease of the patient P.

Here, the controlling function 131 derives the agreement probability between the MDT and the patient P for each of a plurality of treatment plans for the disease on the basis of the preference of the patient P for each of the treatment plans for the disease obtained from the first information and the preference of the MDT for each of the treatment plans for the disease obtained from the second information. The agreement probability is calculated by the following Expression (1):

$$\text{AGREEMENT PROBABILITY} = \sum_{i=1}^{n} p_i^D \times p_i^P \quad (1)$$

In examples illustrated in FIG. 3A and FIG. 3B, the probabilities that the MDT chooses "surgery (SAVR)", "catheterization (TAVI)", "medication", and "no treatment" are expressed respectively as $p_1^D$, $p_2^D$, $p_3^D$, and $p_4^D$ and the probabilities that the patient P chooses "SAVR", "TAVI", "medication", and "no treatment" are expressed respectively as $p_1^P$, $p_2^P$, $p_3^P$, and $p_4^P$. In Expression (I), i represents an integer of 1 to 4. The probability $p_i^D$ about the preference of the MDT is obtained by statistically processing the aforementioned second information. In addition, the preference and the probability $p_i^D$ for the MDT are obtained by inputting the aforementioned second information to a learned model obtained by machine learning. The probability $p_i^P$ about the preference of the patient P is obtained by statistically processing the aforementioned first information. In addition, the preference and the probability $p_i^P$ for the patient P are obtained by inputting the aforementioned first information to the learned model obtained by machine learning.

For example, it is assumed that the probabilities $p_1^D$, $p_2^D$, $p_3^D$, and $p_4^D$ are "0.2", "0.2", "0.6", and "0.1", respectively and the probabilities $p_1^P$, $p_2^P$, $p_3^P$, and $p_4^P$ are "0.3", "0.5", "0.2", and "0.1", respectively. In this case, the value of the agreement probability that the MDT and the patient P agree is "0.29 (29%)" according to Expression (1). The value of the agreement probability derived by the controlling function 131 is reflected by a presenting process to be described below.

Note that the controlling function 131 may predict the patient P's decision and the MDT's decision after excluding the treatment plan that is unsuitable for the patient P. For example, if the drug to be used in the medication for the patient is incompatible with the drug taken by the patient P for his basal disease, the controlling function 131 excludes the medication. For example, if the patient P is a child and the surgery is not a good option, the controlling function 131 excludes the surgery. In this case, the controlling function 131 predicts the patient P's decision and the MDT's decision after excluding the treatment plan that is unsuitable for the patient P among the treatment plans that the MDT may choose from the first information.

Step S102 in FIG. 2 is a step where the processing circuitry 130 calls the computer program corresponding to the presenting function 132 from the storage circuitry 120 and executes the computer program. At step S102, the presenting function 132 performs the presenting process. Specifically, the presenting function 132 causes the display of the terminal 20 of the MDT and the display of the terminal 10 of the patient P's doctor to display the information based on the result of the prediction by the controlling function 131.

FIG. 4 illustrates one example of the screen presented to the MDT and the patient P's doctor. For example, in the case where the controlling function 131 performs the prediction about a plurality of the patients P, the presenting function 132 causes the terminals 10 and 20 to display a list of information based on the result of the prediction by the controlling function 131 for each of the patients P. As illustrated in FIG. 4, the screen displays the patient ID and the patient name, which are the identification information for identifying the patient P, the information about the decision making by the patient P and the MDT, and the collision risk. Here, the result of the prediction by the controlling function 131 is displayed in the lower left part of the column where the information about the decision making is displayed. In addition, if the column to display the information about the decision making is empty, it means that the decision making is not performed yet. The collision risk is the information about the coincidence degree between the patient P's decision and the MDT's decision that are predicted by the controlling function 131. That is to say, the presenting function 132 presents the collision risk as the information according to the value of the agreement probability derived by the controlling function 131.

For example, about the patient P with a patient ID "000001", the prediction results about the patient P's decision and the MDT's decision are "TAVI". In this case, since the patient P's decision and the MDT's decision coincide, in the case where the MDT and the patient P make decisions, the possibility that the MDT and the patient P agree on the treatment plan is high.

On the other hand, about the patient P with a patient ID "000002", the prediction result of the patient P's decision is "SAVR" and the prediction result of the MDT's decision is "TAVI". In this case, since the patient P's decision and the MDT's decision do not coincide, the possibility that the MDT and the patient P agree on the treatment plan is low. In this case, the screen displays a mark expressing a first collision risk while associating this mark with the patient ID "000002". For example, if the agreement probability derived by the controlling function 131 is less than or equal to a first threshold, the mark expressing the first collision risk (circular mark illustrated in FIG. 4) is displayed.

In addition, about the patient P with a patient ID "000004", the prediction result of the patient P's decision is "medication" and the prediction result of the MDT's decision is "TAVI". In this case, since the patient P's decision and the MDT's decision do not coincide, the possibility that the MDT and the patient P agree on the treatment plan is low. In this case, the screen displays a mark expressing a second collision risk while associating this mark with the patient ID "000004". For example, if the value of the agreement probability derived by the controlling function 131 (for example, "0.29 (29%)") is less than or equal to a second threshold, which is lower than the first threshold, a mark expressing a second collision risk (triangular mark illustrated in FIG. 4) is displayed. The second collision risk expresses the probability that they agree is lower than the first collision risk.

Here, if the patient P's decision and the MDT's decision that are predicted by the controlling function 131 do not coincide, the presenting function 132 presents a recommended process that should be performed by at least one of the MDT and the patient P's doctor on the basis of process information that is described below.

Figure 5:
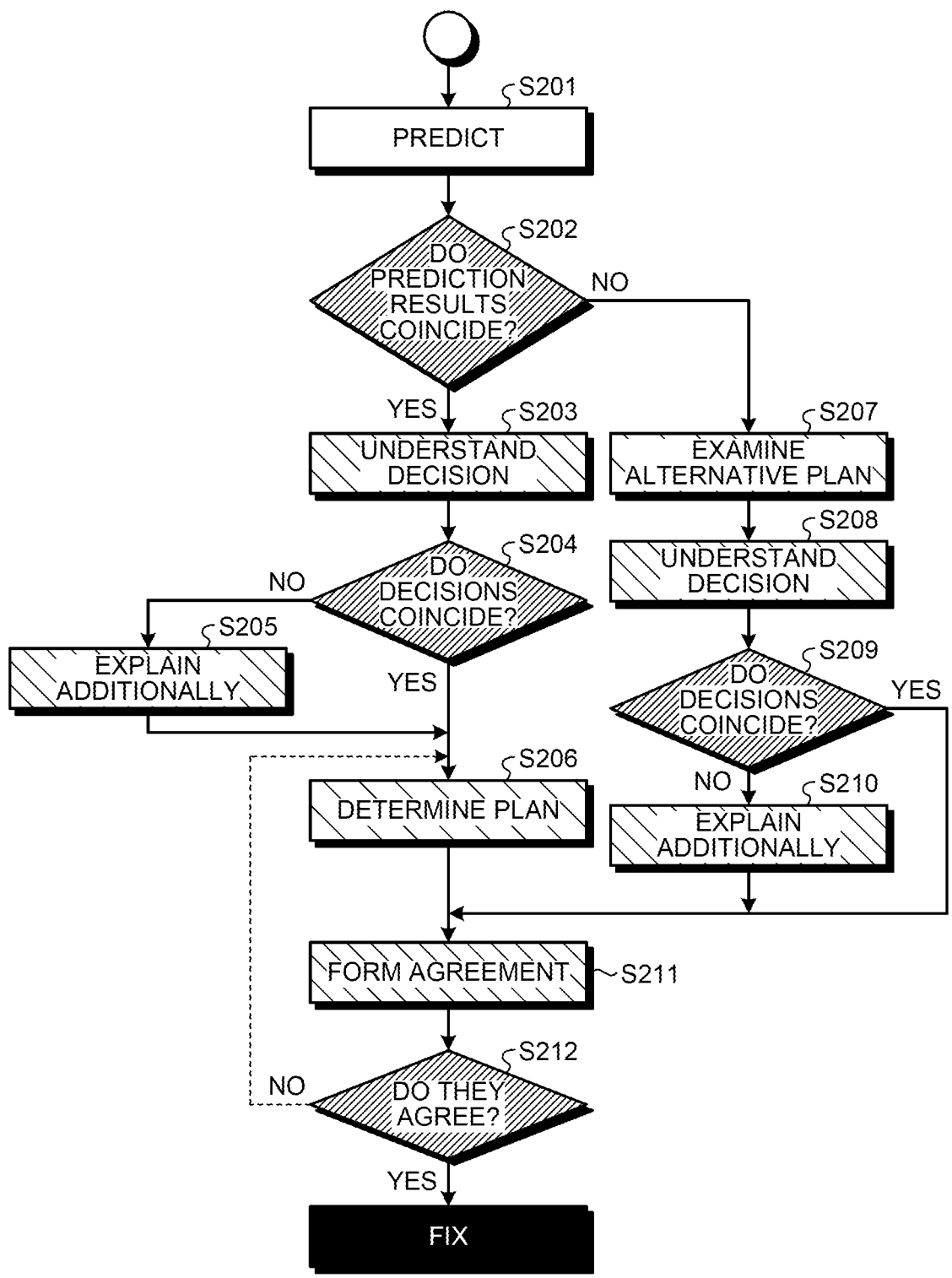
FIG. 5 illustrates one example of process information.

For example, the storage circuitry 120 stores therein the process information expressing the procedure of the process after the controlling function 131 predicts the MDT's decision and the patient P's decision and before the MDT and the patient P agree on the treatment plan. FIG. 5 illustrates one example of the process information.

In FIG. 5, for example, the controlling function 131 predicts the MDT's decision and the patient P's decision (step S201). Here, if the prediction results of the controlling function 131 coincide (Yes at step S202), the decision of the patient P is understood as the recommended process that should be performed by the patient P's doctor (step S203). If the patient P agrees on the treatment plan suggested by the MDT at step S203 and their decisions coincide (Yes at step S204), the treatment plan is determined as the recommended process that should be performed by the MDT (step S206). On the other hand, if the patient P does not agree on the treatment plan suggested by the MDT at step S203 and their decisions do not coincide (No at step S204), additional explanation is made to the patient P as the recommended process that should be performed by the patient P's doctor (step S205) and then, the process advances to step S206. Then, as the recommended process that should be performed by the patient P's doctor, the agreement of the patient P is formed (step S211) and if the patient P agrees on the treatment plan determined by the MDT at step S206 (Yes at step S212), the treatment plan is fixed. Note that if the MDT and the patient P do not agree (No at step S212), the process returns to step S206 and the MDT determines the treatment plan again.

If the results of the prediction by the controlling function 131 do not coincide (No at step S202), an alternative plan for the treatment is examined as the recommended process that should be performed by the MDT (step S207) and then, the decision of the patient P is understood as the recommended process that should be performed by the patient P's doctor (step S208). Specifically, the doctor in charge presents the alternative plan suggested by the MDT at step S207 to the patient P and understands the patient P's decision. If the patient agrees on the alternative plan of the MDT at step S208 and their decisions coincide (Yes at step S209), the process advances to step S211 and step S212. If the patient does not agree on the alternative plan of the MDT at step S208 and their decisions do not coincide (No at step S209), additional explanation is made to the patient P as the recommended process that should be performed by the patient P's doctor (step S210) and then, the process advances to step S211 and step S212.

Here, the recommended process that should be performed by the patient P's doctor is updated as the first information and the recommended process that should be performed by the MDT is updated as the second information. FIG. 6 illustrates one example of the screen presented to the MDT and the patient P's doctor. As illustrated in FIG. 6, the screen also displays recommended actions. Here, the recommended actions are displayed when the patient P's decision and the MDT's decision predicted by the controlling function 131 do not coincide, and each recommended action corresponds to the information expressing the recommended process that should be performed by at least one of the MDT and the patient P's doctor.

The presenting function 132 performs the display of the recommended process together with the information based on the result of the prediction by the controlling function 131. Here, the presenting function 132 updates the display on the screen. For example, upon the reception of the information expressing that the currently presented recommended process is already performed, the presenting function 132 presents the next recommended process on the basis of the process information.

Specifically, about the patient P with the patient ID "000002", the prediction result "SAVR" of the patient P's decision and the prediction result "TAVI" of the MDT's decision do not coincide; therefore, for example, the process at step S207 "examine alternative plan" is recommended. In this case, the screen displays the recommended action "MDT: examine alternative plan" expressing the examination of the alternative plan for the treatment as the recommended process that should be performed by the MDT while associating this process with the patient ID "000002".

In addition, about the patient P with the patient ID "000004", the prediction result "medication" of the patient P's decision and the prediction result "TAVI" of the MDT's decision do not coincide; therefore, the process at step S207 "examine alternative plan" and the process at step S208 "understand decision" are recommended and carried out. Then, after the patient P with the patient ID "000004" agrees on the alternative plan of the MDT, the process at step S210 "explain additionally" is recommended and carried out and subsequently, the process at step S211 "form agreement" is recommended. In this case, the screen displays the information "TAVI" about the MDT's decision making and also displays the recommended action "doctor in charge: form agreement" expressing the agreement formation of the patient P as the recommended process that should be performed by the patient P's doctor, while associating these pieces of information with the patient ID "000004".

On the other hand, about the patient P with the patient ID "000001", the prediction result "TAVI" of the patient P's decision and the prediction result "TAVI" of the MDT's decision coincide; therefore, for example, the process at step S203 "understand decision", the process at step S206 "determine plan", and the process at step S211 "form agreement" are recommended and carried out sequentially and the treatment plan is fixed. In this case, the screen displays the information "TAVI" about the patient P's decision making and the information "TAVI" about the MDT's decision making, and displays the recommended action "fix" expressing the fixing of the treatment plan, while associating these pieces of information with the patient ID "000001".

Additionally, about the patient P with a patient ID "000003", the prediction result "SAVR" of the patient P's decision and the prediction result "SAVR" of the MDT's decision coincide; therefore, for example, the process at step S203 "understand decision" is recommended. In this case, the screen displays the recommended action "doctor in charge: understand decision" expressing the understanding of the patient P's decision as the recommended process that should be performed by the patient P's doctor, while associating this process with the patient ID "000003".

In addition, about the patient P with a patient ID "000005", the prediction result "SAVR" of the patient P's decision and the prediction result "SAVR" of the MDT's decision coincide; therefore, for example, the process at step S203 "understand decision" is recommended and performed, and then the process at step S206 "determine plan" is recommended. In this case, the screen displays the recommended action "MDT: determine plan" expressing the determination of the treatment plan as the recommended process that should be performed by the MDT, while associating this process with the patient ID "000005".

Note that about the patient P with a patient ID "000006", the prediction result "SAVR" of the patient P's decision and the prediction result "SAVR" of the MDT's decision coincide; however, the patient P does not agree on the treatment plan suggested by the MDT and their decisions do not coincide. Therefore, for example, the process at step S205 "explain additionally" is recommended. In this case, the screen displays the recommended action "doctor in charge: explain additionally" expressing the additional explanation to the patient P as the recommended process that should be performed the patient P's doctor, while associating this process with the patient ID "000006".

In the above description, in the medical treatment support apparatus 100 according to the first embodiment, about the treatment plan for the disease of the patient P, the controlling function 131 predicts the decision of the patient P and the decision of the MDT who determines the treatment plan for the patient P, and the presenting function 132 presents the information based on the result of the prediction by the controlling function 131 to the MDT and the doctor in charge of confirming the patient P's decision. Thus, the reconsideration of the treatment plan can be avoided. Therefore, in the medical treatment support apparatus 100 according to the first embodiment, the MDT can perform the treatment in accordance with the treatment plan that satisfies the patient P. In addition, in the medical treatment support apparatus 100 according to the first embodiment, the patient P's doctor does not need to talk about the treatment plan with the patient P again or the MDT does not need to have another discussion, so that the burden on the decision making can be reduced.

Note that in the case of displaying the list, the presenting function 132 may display the list in the order of the larger difference between the decisions. For example, in the case of displaying the list, the presenting function 132 changes the order of displaying the patients P in accordance with the coincidence degree between the patient P's decision and the MDT's decision predicted by the controlling function 131. In the example illustrated in FIG. 4, in the case of giving priority on the display of the mark expressing the collision risk, the information about the patients P with the patient IDs of "000004", "000006", and "000002" is displayed with priority.

In addition, in the case of displaying the list, the presenting function 132 may display the list in the order of higher emergency of the treatment. For example, in the case of displaying the list, the presenting function 132 changes the order of displaying the patients P in accordance with the degree of emergency of the treatment plan that is predicted by the controlling function 131 to have the high possibility of being chosen by the MDT from the first information.

In addition, as the update of the screen display, the presenting function 132 updates the display of the recommended action; however, the presenting function 132 may update the display of the collision risk in addition to the recommended action. For example, about the patient P with the patient ID "000002", the collision risk is displayed; however, if the agreement probability is calculated again about the alternative plan determined by the MDT and the agreement probability becomes higher than the first threshold, the collision risk may be eliminated. Thus, the doctor in charge can understand that the collision risk is reduced largely and understand the patient P's decision.

Second Embodiment

In the medical treatment support apparatus 100 according to a second embodiment, the order of presenting the process to be performed by the MDT and the process to be performed by the patient P's doctor is determined based on the agreement probability. That is to say, the presenting function 132 presents the order of the recommended processes as the information according to the value of the agreement probability derived by the controlling function 131.

Specifically, at step S101, the controlling function 131 calculates a first probability that the MDT and the patient P agree in the case where the MDT makes a decision first, and a second probability that the MDT and the patient P agree in the case where the patient P makes a decision first on the basis of the preference and the acceptable range for the patient P for each of the treatment plans for the disease obtained from the first information and the preference and the acceptable range for the MDT for each of the treatment plans for the disease obtained from the second information. At step S102, the presenting function 132 determines the order of presenting the process to be performed by the MDT and the process to be performed by the patient P's doctor on the basis of the first probability and the second probability.

In the example illustrated in FIG. 7, the probability is not considered regarding the preference and the acceptable range, and as for the preference, whether the option is chosen is considered and as for the acceptable range, whether the option is acceptable is considered. For example, the option where the probability ($p_i^D$ or $p_i^P$) about the preference described above is more than or equal to a threshold A is expressed in FIG. 7 as a circle representing that this option can be chosen. In another example, the option where the probability ($p_i^D$ or $p_i^P$) about the preference described above is more than or equal to a threshold B is expressed in FIG. 7 as half-tone dot meshing representing that the option is acceptable. The threshold A is a threshold set to determine whether the option can be chosen, and the threshold B is a threshold set to determine whether the option is acceptable. The controlling function 131 calculates the agreement probability that the MDT and the patient P agree in the case where the MDT makes a decision first, and the agreement probability that the MDT and the patient P agree in the case where the patient P makes a decision first. The agreement probability is calculated based on the following Expression (2):

$$\text{AGREEMENT PROBABILITY} = \frac{\text{THE NUMBER OF OPTIONS INCLUDED IN MY ACCEPTABLE RANGE AND IN THE COUNTERPART'S ACCEPTABLE RANGE}}{\text{THE NUMBER OF OPTIONS INCLUDED IN MY ACCEPTABLE RANGE}} \quad (2)$$

In the example illustrated in FIG. 7, among the four options "SAVR", "TAVI", "medication", and "no treatment", the MDT can accept the two options "SAVR" and "TAVI"; therefore, the number of options included in the acceptable range for the MDT is "2". In addition, among the four options "SAVR", "TAVI", "medication", and "no treatment", the patient P can accept the three options "TAVI", "medication", and "no treatment"; therefore, the number of options included in the acceptable range for the patient P is "3".

Here, in the case where the MDT makes a decision first, the number of options in the acceptable range for the MDT and the acceptable range for the patient P is just one, which is "TAVI"; therefore, the value of the agreement probability that the MDT and the patient P agree in the case where the MDT makes a decision first is "0.5 (50%)" from Expression (2). This agreement probability is one example of the first probability. In the case where the patient P makes a decision first, the number of options in the acceptable range for the MDT and the acceptable range for the patient P in the numerator in Expression (2) is just one, which is "TAVI"; therefore, the value of the agreement probability that the MDT and the patient P agree in the case where the patient P makes a decision first is "0.33 (33%)" from Expression (2). This agreement probability is one example of the second probability.

In this case, the presenting function 132 determines that, out of the process to be performed by the MDT and the process to be performed by the patient P's doctor, the process is performed by the MDT with priority on the basis of the first probability and the second probability, and causes the displays of the terminals 10 and 20 to present that it is better to perform the process by the MDT with priority. Specifically, since the agreement probability is higher when the patient P makes a decision after the MDT makes a decision, for example, the presenting function 132 presents the process at step S207 "examine alternative plan" as the recommended process as illustrated in the flowchart in FIG. 5.

In the example illustrated in FIG. 8, the choosing probability is considered as for the preference, and whether the option is acceptable is considered as for the acceptable range. Here, for example, the option where the probability ($p_i^D$ or $p_i^P$) about the preference is more than or equal to the threshold is expressed in FIG. 8 as the half-tone dot meshing representing that the option is acceptable. The controlling function 131 calculates the agreement probability $p^D$ that the MDT and the patient P agree in the case where the MDT makes a decision first and the agreement probability $p^P$ that the MDT and the patient P agree in the case where the patient P makes a decision first. The agreement probabilities $p^D$ and $p^P$ are calculated by the following Expressions (3) and (4), respectively.

$$P^D = \sum_{i=1}^{n} p_i^D \times u(p_i^P) \quad u(x) = \begin{cases} 0 (x < a) \\ 1 (x \geq a) \end{cases} \quad (3)$$

$$P^P = \sum_{i=1}^{n} p_i^P \times u(p_i^D) \quad u(x) = \begin{cases} 0 (x < a) \\ 1 (x \geq a) \end{cases} \quad (4)$$

In the example illustrated in FIG. 8, the probability is considered as for the preference. For example, it is assumed that the MDT can accept the options "SAVR" and "TAVI" among the four options "SAVR", "TAVI", "medication", and "no treatment", and the patient P can accept the options "TAVI", "medication", and "no treatment" among the options "SAVR", "TAVI", "medication", and "no treatment". In the example illustrated in FIG. 8, in a manner similar to the first embodiment, the probabilities that the MDT chooses the options "SAVR", "TAVI", "medication", and "no treatment" are respectively expressed as $p_1^D$, $p_2^D$, $p_3^D$, and $p_4^D$, and the probabilities that the patient P chooses the options "SAVR", "TAVI", "medication", and "no treatment" are respectively expressed as $p_1^P$, $p_2^P$, $p_3^P$, and $p_4^P$.

For example, it is assumed that the probabilities $p_1^D$, $p_2^D$, $p_3^D$, and $p_4^D$ are "0.4", "0.4", "0.1", and "0.1", respectively and the probabilities $p_1^P$, $p_2^P$, $p_3^P$, and $p_4^P$ are "0.1", "0.6", "0.2", and "0.1", respectively. In Expressions (3) and (4), a threshold a about the acceptable range is "0.2". In this case, the value of the agreement probability $p^D$ that the MDT and the patient P agree in the case where the MDT makes a decision first is "$p^D$=0.4×0+0.4×1+0.1×1+0.1×0=0.5 (50%)" according to Expression (3). The agreement probability $p^D$ is one example of the first probability. The value of the agreement probability $p^P$ that the MDT and the patient P agree in the case where the patient P makes a decision first is "$p^P$=0.1×1+0.6×1+0.2×0+0.1×0=0.7 (70%)" according to Expression (4). The agreement probability $p^P$ is one example of the second probability.

In this case, the presenting function 132 determines that, out of the process to be performed by the MDT and the process to be performed by the patient P's doctor, the process is performed by the patient P's doctor with priority on the basis of the first probability and the second probability, and causes the displays of the terminals 10 and 20 to present that it is better to perform the process by the patient P's doctor with priority. Specifically, since the agreement probability is higher when the MDT makes a decision after the patient P makes a decision, for example, unlike the flowchart in FIG. 5, if the prediction results do not coincide, the presenting function 132 presents "understand decision" at step S203 where the doctor in charge presents the MDT's suggestion to the patient and finds out the patient's decision as the recommended process. If the coincidence is not obtained yet, "examine alternative plan" to recommend the process at step S207 is presented.

In the example illustrated in FIG. 9, the choosing probability is considered as for the preference and the probability that the option is acceptable is considered as for the acceptable range. The controlling function 131 calculates the agreement probability $p^D$ that the MDT and the patient P agree in the case where the MDT makes a decision first, and the agreement probability $p^P$ that the MDT and the patient P agree in the case where the patient P makes a decision first. The agreement probabilities $p^D$ and $p^P$ are calculated by the following Expressions (5) and (6), respectively.

$$P^D = \sum_{i=1}^{n} p_i^D \times q_i^P \tag{5}$$

$$P^P = \sum_{i=1}^{n} p_i^D \times q_i^P \tag{6}$$

In the example illustrated in FIG. 9, the probability is considered as for the preference and the acceptable range. For example, in the example illustrated in FIG. 9, it is assumed that the MDT can accept the options "SAVR" and "TAVI" among the four options "SAVR", "TAVI", "medication", and "no treatment", and the patient P can accept the options "TAVI" and "medication" among the four options "SAVR", "TAVI", "medication", and "no treatment", in a manner similar to FIG. 8. In the example illustrated in FIG. 9, in a manner similar to the first embodiment, the probabilities that the MDT chooses the options "SAVR", "TAVI", "medication", and "no treatment" are respectively expressed as $p_1^D$, $p_2^D$, $p_3^D$, and $p_4^D$, and the probabilities that the patient P chooses the options "SAVR", "TAVI", "medication", and "no treatment" are respectively expressed as $p_1^P$, $p_2^P$, $p_3^P$, and $p_4^P$. Moreover, in the example illustrated in FIG. 9, the probabilities that the MDT can accept the options "SAVR", "TAVI", "medication", and "no treatment" are respectively expressed as $q_1^D$, $q_2^D$, $q_3^D$, and $q_4^D$, and the probabilities that the patient P can accept the options "SAVR", "TAVI", "medication", and "no treatment" are respectively expressed as $q_1^P$, $q_2^P$, $q_3^P$, and $q_4^P$. The probability $p_i^D$ about the preference of the MDT and the probability $q_i^D$ about the acceptable range for the MDT can be obtained by statistically processing the aforementioned second information. In addition, the preference and the probability $p_i^D$ for the MDT can be obtained by inputting the aforementioned second information to the learned model obtained by the machine learning. Moreover, the probability $p_i^P$ about the preference of the patient P and the probability $q_i^P$ about the acceptable range for the patient P can be obtained by statistically processing the aforementioned first information. In addition, the preference and the probability $p_i^D$ for the patient P can be obtained by inputting the aforementioned first information to the learned model obtained by the machine learning.

For example, it is assumed that the probabilities $p_1^D$, $p_2^D$, $p_3^D$, and $p_4^D$ are "0.4", "0.4", "0.1", and "0.1", respectively and the probabilities $q_1^D$, $q_2^D$, $q_3^D$, and $q_4^D$ are "0.7", "0.8", "0.4", and "0.2", respectively. It is assumed that the $p_1^P$, $p_1^P$, $p_3^P$, and $p_4^P$ are "0.1", "0.6", "0.2", and "0.1", respectively and the probabilities $q_1^P$, $q_2^P$, $q_3^P$, and $q_4^P$ are "0.3", "0.9", "0.6", and "0.1", respectively. In view of this, the value of the agreement probability $p^D$ that the MDT and the patient P agree in the case where the MDT makes a decision first is "$p^D$=0.4×0.3+0.4×0.9+0.1×0.6+0.1×0.6=0.6 (60%)" from Expression (5). The agreement probability $p^D$ is one example of the first probability. Moreover, the value of the agreement probability $p^P$ that the MDT and the patient P agree in the case where the patient P makes a decision first is "$p^P$=0.1×0.7+0.6×0.8+0.2×0.4+0.1×0.2=0.65 (65%)" from Expression (6). The agreement probability $p^P$ is one example of the second probability.

In this case, the presenting function 132 determines that, out of the process to be performed by the MDT and the process to be performed by the patient P's doctor, the process is performed by the patient P's doctor with priority on the basis of the first probability and the second probability, and causes the displays of the terminals 10 and 20 to present that it is better to perform the process by the patient P's doctor with priority. Specifically, the presenting function 132 performs the process described in the example illustrated in FIG. 8.

Third Embodiment

In the medical treatment support apparatus 100 according to a third embodiment, the order of presenting the process to be performed by the MDT and the process to be performed by the patient P's doctor is determined based on the agreement probability for each number of options chosen from the treatment plans for the disease.

In an example illustrated in FIG. 10, the choosing probability is considered as for the preference, and whether the option is acceptable is considered as for the acceptable range. Here, for example, the option where the probability ($p_i^D$ or $p_i^P$) about the preference is more than or equal to the threshold is expressed in FIG. 10 as the half-tone dot meshing representing that the option is acceptable. The controlling function 131 calculates the agreement probability $p^D$ that the MDT and the patient P agree in the case where the MDT chooses two options first and the agreement probability $p^P$ that the MDT and the patient P agree in the case where the patient P chooses two options first. The agreement probabilities $p^D$ and $p^P$ are calculated by the following Expressions (7) and (8), respectively.

$$P^D = \sum_{i=1}^{n} \sum_{j=1, j\neq 1}^{n} p_i^D \times \left\{\frac{p_j^D}{1-p_i^D}\right\} \times u(p_i^P, p_j^P) \; u(x, y) = \tag{7}$$

$$\begin{cases} 1(x \geq a \text{ OR } y \geq a) \\ 0(x < a \text{ AND } y < a) \end{cases}$$

$$P^P = \sum_{i=1}^{n} \sum_{j=1, j\neq 1}^{n} p_i^P \times \left\{\frac{p_j^P}{1-p_i^P}\right\} \times u(p_i^D, p_j^D) \; u(x, y) = \tag{8}$$

$$\begin{cases} 1(x \geq a \text{ OR } y \geq a) \\ 0(x < a \text{ AND } y < a) \end{cases}$$

In the example illustrated in FIG. 10, the number of options is considered additionally in the case where the collision is expected (in the case where the agreement probability is low). For example, it is assumed that and the MDT can accept the option "SAVR" among the four options "SAVR", "TAVI", "medication", and "no treatment", and the patient P can accept the option "medication" among the four options "SAVR", "TAVI", "medication", and "no treatment". Moreover, in the example illustrated in FIG. 10, in a manner similar to the first embodiment, the probabilities that the MDT chooses the options "SAVR", "TAVI", "medication", and "no treatment" are respectively expressed as $p_1^D$, $p_2^D$, $p_3^D$, and $p_4^D$, and the probabilities that the patient P chooses the options "SAVR", "TAVI", "medication", and "no treatment" are respectively expressed as $p_1^P$, $p_2^P$, $p_3^P$, and $p_4^P$.

For example, it is assumed that the probabilities $p_1^D$, $p_2^D$, $p_3^D$, and $p_4^D$ are "0.5", "0.3", "0.1", and "0.1", respectively and the probabilities $p_1^P$, $p_2^P$, $p_3^P$, and $p_4^P$ are "0.3", "0.1", "0.5", and "0.1", respectively. Here, according to the controlling function 131 using Expressions (3) and (4), the agreement probability $p^D$ that the MDT and the patient P agree in the case where the MDT chooses one option first is "0.1" and the agreement probability $p^P$ that the MDT and the patient P agree in the case where the patient P chooses one option first is "0.3". Since the agreement probability is low, for example, the controlling function 131 calculates the agreement probability $p^D$ that the MDT and the patient P agree in the case where the MDT chooses two options first and the agreement probability $p^P$ that the MDT and the patient P agree in the case where the patient P chooses two options first.

Here, in Expressions (7) and (8), a is "0.4". Moreover, the value of the agreement probability $p^D$ that the MDT and the patient P agree in the case where the MDT chooses two options first is "$p^D$=0.5×(0.1/(1−0.5))×1)+0.3×(0.1/(1−0.3))×1+0.1×1+0.1×(0.1/(1−0.1))×1)=0.254 (25.4%)" from Expression (7). The agreement probability $p^D$ is one example of the first probability. Moreover, the value of the agreement probability $p^P$ that the MDT and the patient P agree in the case where the patient P chooses two options first is "$p^D$=0.3×1+0.1×(0.3/(1−0.1))×1)+0.1×(0.3/(1−0.1))× 1+0.5×(0.3/(1−0.5))×1)+0.1×(0.3/(1−0.1))×1)=0.667 (66.7%)" from Expression (8). The agreement probability $p^P$ is one example of the second probability.

In this case, the presenting function 132 determines that, out of the process to be performed by the MDT and the process to be performed by the patient P's doctor, the process is performed by the patient P's doctor with priority on the basis of the first probability and the second probability for each number of options, and causes the displays of the terminals 10 and 20 to present that it is better to perform the process by the patient P's doctor with priority.

For example, FIG. 11 illustrates one example of the screen that is presented to the MDT and the patient P's doctor in the case where two processes to be performed by the MDT are chosen. In the example illustrated in FIG. 11, about the patient P with the patient ID "000002", the prediction result "SAVR" of the patient P's decision and the prediction result "TAVI" of the MDT's decision do not coincide; therefore, for example, the process at step S207 is recommended. In this case, the screen displays the recommended action "MDT: examine alternative plans (2)" expressing the suggestion of two alternative plans as the recommended process that should be performed by the MDT, while associating this process with the patient ID "000002".

Fourth Embodiment

In the medical treatment support apparatus 100 according to a fourth embodiment, as illustrated in FIG. 12A and FIG. 12B, the choosing probability is considered as for the preference and the conditional choosing probability is used as the probability that the option is acceptable as for the acceptable range.

In this case, the controlling function 131 calculates the probability $p^D$ that the MDT and the patient P agree in the case where the MDT makes a decision first, and the probability $p^D$ that the MDT and the patient P agree in the case where the patient P makes a decision first. The agreement probabilities $p^D$ and $p^P$ are calculated by the following Expressions (9) and (10), respectively.

$$P^D = \sum_{i=1}^{n} p^D(i) \times p_i^P(i) \quad (9)$$

$$P^P = \sum_{i=1}^{n} p^P(i) \times p_i^D(i) \quad (10)$$

In the examples illustrated in FIG. 12A and FIG. 12B, the acceptable range is predicted based on the conditional probability. In the examples illustrated in FIG. 12A and FIG. 12B, "treatment A", "treatment B", and "treatment C" correspond to the aforementioned "SAVR", "TAVI", and "medication" described above, respectively. For example, the probabilities $p^D(i)$ that the MDT chooses "treatment A", "treatment B", and "treatment C" before the presentation are respectively "0.1", "0.2", and "0.7". Moreover, the probabilities $p^P(i)$ that the patient P chooses "treatment A", "treatment B", and "treatment C" before the presentation are respectively "0.3", "0.6", and "0.1".

The conditional choosing probabilities $p_i^D(j)$ that the MDT chooses "treatment A", "treatment B", and "treatment C" after the patient P presents "treatment A" are respectively "0.6", "0.1", and "0.3" as the probabilities that the MDT can accept "treatment A", "treatment B", and "treatment C". Moreover, the conditional choosing probabilities $p_i^D(j)$ that the MDT chooses "treatment A", "treatment B", and "treatment C" after the patient P presents "treatment B" are respectively "0.2", "0.2", and "0.6" as the probabilities that the MDT can accept "treatment A", "treatment B", and "treatment C". The conditional choosing probabilities $p_i^D(j)$ that the MDT chooses "treatment A", "treatment B", and "treatment C" after the patient P presents "treatment C" are respectively "0.2", "0.0", and "0.8" as the probabilities that the MDT can accept "treatment A", "treatment B", and "treatment C".

The conditional choosing probabilities $p_i^P(j)$ that the patient P chooses "treatment A", "treatment B", and "treatment C" after the MDT presents "treatment A" are respectively "0.2", "0.6", and "0.2" as the probabilities that the patient P can accept "treatment A", "treatment B", and "treatment C". The conditional choosing probabilities $p_i^P(j)$ that the patient P chooses "treatment A", "treatment B", and "treatment C" after the MDT presents "treatment B" are respectively "0.2", "0.8", and "0.0" as the probabilities that the patient P can accept "treatment A", "treatment B", and "treatment C". The conditional choosing probabilities $p_i^P(j)$ that the patient P chooses "treatment A", "treatment B", and "treatment C" after the MDT presents "treatment C" are respectively "0.4", "0.6", and "0.0" as the probabilities that the patient P can accept "treatment A", "treatment B", and "treatment C".

In Expressions (9) and (10), i represents an integer of 1 to 3, and i=1, 2, 3 correspond to "treatment A", "treatment B", and "treatment C", respectively. The conditional choosing probabilities $p^D(i)$ and $p_i^D(j)$ of the MDT are obtained by statistically processing the aforementioned second information. Alternatively, the conditional choosing probabilities $p^D(i)$ and $p_i^D(j)$ of the MDT are obtained by inputting the aforementioned second information to the learned model obtained by the machine learning. The conditional choosing probabilities $p^P(i)$ and $p_i^P(j)$ of the patient P are obtained by statistically processing the aforementioned first information.

Alternatively, the conditional choosing probabilities $p_i^P(i)$ and $p_i^P(j)$ of the patient P are obtained by inputting the aforementioned first information to the learned model obtained by the machine learning.

In view of this, the value of the agreement probability $p^D$ that the MDT and the patient P agree in the case where the MDT makes a decision first is "$p^D=0.1\times 0.2+0.2\times 0.8+0.7\times 0.0=0.18$ (18%)" from Expression (9). The agreement probability $p^D$ is one example of the first probability. The value of the agreement probability $p^P$ that the MDT and the patient P agree in the case where the patient P makes a decision first is "$p^P=0.3\times 0.6+0.6\times 0.2+0.1\times 0.8=0.38$ (38%)" from Expression (10). The agreement probability $p^P$ is one example of the second probability. In FIG. 12A and FIG. 12B, the conditional choosing probabilities used in Expressions (9) and (10) are illustrated as the half-tone dot meshing.

In this case, the presenting function 132 determines that, out of the process to be performed by the MDT and the process to be performed by the patient P's doctor, the process is performed by the patient P's doctor with priority on the basis of the first probability and the second probability, and causes the displays of the terminals 10 and 20 to present that it is better to perform the process by the patient P's doctor with priority. Specifically, the presenting function 132 performs the process described in the example illustrated in FIG. 8.

In addition, in the medical treatment support apparatus 100 according to the fourth embodiment, in a manner similar to the third embodiment, the order of presenting the process to be performed by the MDT and the process to be performed by the patient P's doctor may be determined based on the agreement probability for each number of options chosen from the treatment plans for the disease.

In this case, the controlling function 131 calculates the agreement probability $p^D$ that the MDT and the patient P agree in the case where the MDT chooses the two options first and the agreement probability $p^P$ that the MDT and the patient P agree in the case where the patient P chooses the two options first. The agreement probabilities $p^D$ and $p^P$ are calculated by the following Expressions (11) and (12), respectively.

$$P^D = \sum_{i=1}^{n} \sum_{j=1, j\neq i}^{n} p_i^D \times \left\{\frac{p_j^D}{1-p_i^D}\right\} \times \{p_i^P(i) + p_i^P(j)\} \quad (11)$$

$$P^P = \sum_{i=1}^{n} \sum_{j=1, j\neq i}^{n} p_i^P \times \left\{\frac{p_j^P}{1-p_i^P}\right\} \times \{p_i^D(i) + p_i^D(j)\} \quad (12)$$

Moreover, the number of options may be considered additionally in the case where the collision is expected (in the case where the agreement probability is low) in the examples illustrated in FIG. 12A and FIG. 12B. In the case of considering the number of options additionally, all the conditional choosing probabilities are used regardless of the presence or absence of the half-tone dot meshing in FIG. 12A and FIG. 12B.

In view of this, the value of the agreement probability $p^D$ that the MDT and the patient P agree in the case where the MDT chooses two options first is "$p^D=0.1\times(0.2/(1-0.1))\times(0.2+0.2)+0.1\times(0.7/(1-0.1))\times(0.2+0.4)+\ldots=0.4$ (40%)" from Expression (11). The agreement probability $p^D$ is one example of the first probability. Moreover, the value of the agreement probability $p^P$ that the MDT and the patient P agree in the case where the patient P chooses two options first is "$p^P=0.3\times(0.6/(1-0.3))\times(0.6+0.1)+0.3\times(0.1/(1-0.3))\times(0.6+0.2)+\ldots=0.585$ (58.5%)" from Expression (12). The agreement probability $p^P$ is one example of the second probability. In this case, the presenting function 132 determines that, out of the process to be performed by the MDT and the process to be performed by the patient P's doctor, the process is performed by the patient P's doctor with priority on the basis of the first probability and the second probability, and causes the displays of the terminals 10 and 20 to present that it is better to perform the process by the patient P's doctor with priority.

Other Embodiments

In addition to the first embodiment to the fourth embodiment that have been described so far, various other embodiments than the first embodiment to the fourth embodiment may be performed.

For example, the decision making of the patient P and the decision making of the MDT are performed at different places and different timings as described above. As a modification of the embodiment, the controlling function 131 may predict the decisions of two of a plurality of, at least three, decision makers including the MDT and the patient P, and the presenting function 132 may present the prediction result about the two.

In this case, the controlling function 131 predicts the decision of subjects who are the patient P or the subjects corresponding to people who are involved with the patient P about the treatment plan for the patient P's disease, and the decision of the MDT who determines the treatment plan for the patient P, and the presenting function 132 presents the information based on the result of the prediction by the controlling function 131 to the MDT and the subjects. Here, the people involved may be the patient P's family, and the patient P's family includes the patient P's father, mother, brothers, sisters, grandparents, spouse, children, and so on. For example, the patient P's decision may be based on the result of the conversation with the patient P's doctor or with the patient P's family, or may be based on any other result.

Figure 13A:
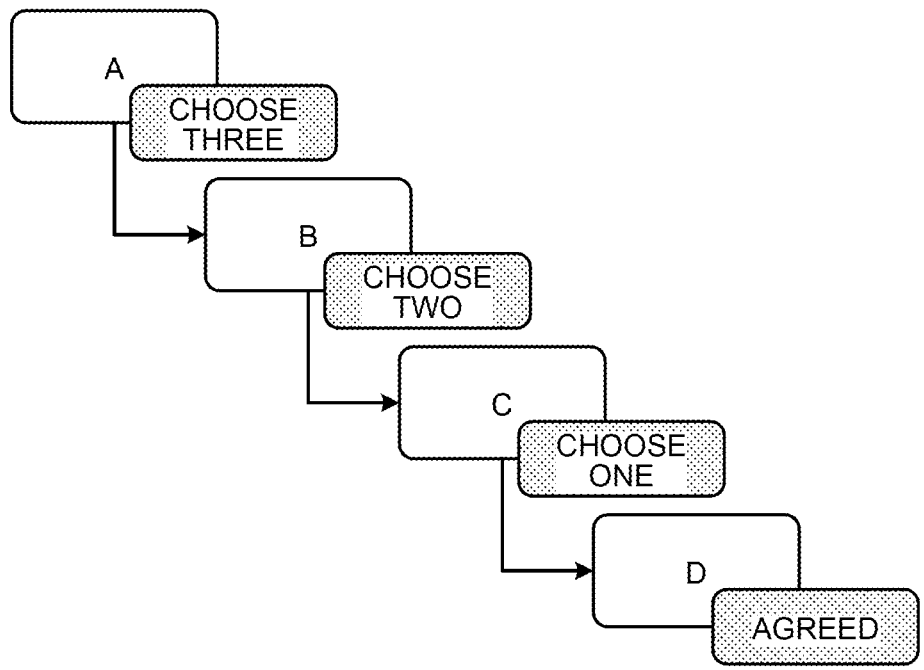
FIG. 13A is a diagram for describing a process by the medical treatment support apparatus according to a modification.

For example, as illustrated in FIG. 13A, in a process A, among the MDT, the patient P, and the patient P's family, the controlling function 131 selects three: the MDT, the patient P, and the patient P's mother. Next, in a process B, among the MDT, the patient P, and the patient P's mother, the controlling function 131 selects two: the MDT and the patient P. Next, in a process C, the controlling function 131 predicts the decisions of the MDT and the patient P and the presenting function 132 presents the information based on the result of the prediction by the controlling function 131 to both the MDT and the patient P. Then, the MDT and the patient P agree on the treatment plan.

Figure 13B:
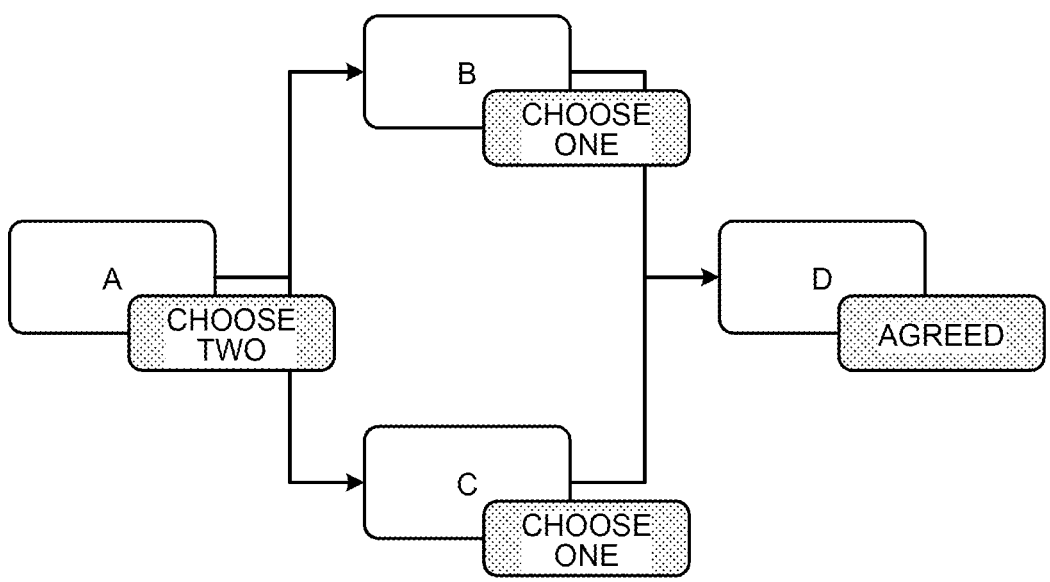
FIG. 13B is a diagram for describing the process by the medical treatment support apparatus according to the modification.

As illustrated in FIG. 13B, in the process A, among the MDT, the patient P, the patient P's family, the controlling function 131 selects two: the MDT, and the patient P's spouse. Next, in the process B, the controlling function 131 predicts the decision of the MDT and in the process C, the controlling function 131 predicts the decision of the patient P's spouse as the patient P's decision and the presenting function 132 presents the information based on the prediction result by the controlling function 131 to both the MDT and the patient P's spouse. Then, the MDT and the patient P's spouse agree on the treatment plan.

Here, in the modification, in the prediction and the presentation of the different two, the number of options about the treatment plan may be changed in a manner similar to the third embodiment and the fourth embodiment.

As a modification of the present embodiment, the presenting function 132 may present the information based on the result of the prediction by the controlling function 131 to the MDT only.

For example, in the case where the information based on the result of the prediction by the controlling function 131 is presented on the display of the terminal 20 of the MDT, the MDT tells the patient P the information directly or tells the patient P the information through the doctor in charge as the communication between the MDT and the patient P. Specifically, the screen on the display of the terminal 20 of the MDT displays the recommended action "the doctor in charge understands the patient's decision" as the recommended process that should be performed by the MDT while associating this process with the patient ID of the patient. In this case, the MDT tells the doctor in charge the information based on the result of the prediction by the controlling function 131, and the doctor in charge having received this information has a meeting with the patient P so as to understand the patient P's decision.

For example, as a modification of the present embodiment, the presenting function 132 may present the information based on the result of the prediction by the controlling function 131 only to the aforementioned subject not through the patient P's doctor. Specifically, the presenting function 132 presents the information based on the result of the prediction by the controlling function 131 only to the patient P or the people involved with the patient P (patient P's family).

For example, in the case where the display of the patient P's terminal presents the information based on the result of the prediction by the controlling function 131, the MDT and the patient P communicate with each other on the system. Specifically, the screen on the display of the patient P's terminal displays the recommended action "understand the decision" as the recommended process that should be performed by the patient P while associating this process with the patient ID of the patient. Here, in the case where the patient P inputs the patient P's decision using the patient P's terminal, the presenting function 132 presents the next recommended process to the MDT. Specifically, the screen on the display of the MDT's terminal 20 displays the recommended action "MDT: determine plan" expressing the determination of the treatment plan as the recommended process that should be performed by the MDT, while associating this process with the patient ID of the patient. Then, the MDT determines the treatment plan.

In this manner, in the case where the information based on the result of the prediction by the controlling function 131 is presented either to the MDT only or to the subject only, the reconsideration of the treatment plan can be avoided by the communication between the MDT and the patient P in the treatment support device 100 according to the modification. Therefore, the MDT can perform the treatment with the treatment plan that satisfies the patient P in the treatment support device 100 according to the modification. Moreover, the treatment support device 100 according to the modification can avoid another discussion in the MDT and accordingly, the burden on the decision making can be reduced.

In the first embodiment, the presenting function 132 presents the collision risk as the information about the coincidence degree between the patient P's decision and the MDT's decision predicted by the controlling function 131; however, the information is not limited to this collision risk. In another example, in a modification of the present embodiment, the presenting function 132 may present a collision risk that is the information about the coincidence degree between the MDT's decision and the subject's decision (the subject is the patient P or the person who is involved with the patient P) predicted by the controlling function 131.

In the first embodiment, the controlling function 131 predicts the patient P's decision and the MDT's decision on the basis of the first information about the decision making by the patient P (information about the tendency of the treatment plan desired by the patient P) and the second information about the decision making by the MDT (information about the tendency of the treatment plan suggested by a medical specialist such as MDT); however, the present invention is not limited to this example. In another example, in a modification of the present embodiment, the controlling function 131 may predict the subject's decision (the subject is the patient P or the person who is involved with the patient P) and the MDT's decision on the basis of the first information about the decision making by the subject and the second information about the decision making by the MDT.

In addition, in the first embodiment, the controlling function 131 derives the agreement probability between the MDT and the patient P for each of the treatment plans for the disease on the basis of the preference of the patient P for each of the treatment plans for the disease obtained from the first information and the preference of the MDT for each of the treatment plans for the disease obtained from the second information, and the presenting function 132 presents the information according to the value of the agreement probability derived by the controlling function 131; however, the present invention is not limited to this example. In another example, in a modification of the present embodiment, the controlling function 131 may derive the agreement probability between the MDT and the subject (the patient P or the person who is involved with the patient P) for each of the treatment plans for the disease on the basis of the preference of the subject for each of the treatment plans for the disease obtained from the first information and the preference of the MDT for each of the treatment plans for the disease obtained from the second information, and the presenting function 132 may present the information according to the value of the agreement probability derived by the controlling function 131.

Moreover, in the first embodiment, in the case where the controlling function 131 performs the prediction about the patients P, the presenting function 132 displays a list of information based on the result of the prediction by the controlling function 131 for each of the patients P; however, the present invention is not limited to this example. In another example, in a modification of the present embodiment, in the case where the controlling function 131 performs the prediction about a plurality of subjects (the patients P or the people who are involved with the patients P), the presenting function 132 may display a list of information based on the result of the prediction by the controlling function 131 for each of the subjects.

Furthermore, in the first embodiment, in the case of displaying a list, the presenting function 132 changes the order of displaying the patients P in accordance with the coincidence degree between the MDT's decision and the patient P's decision predicted by the controlling function 131; however, the present invention is not limited to this example. In another example, in a modification of the present embodiment, in the case of displaying the list, the presenting function 132 may change the order of displaying the subjects (the patients P or the people who are involved with the patients P) in accordance with the coincidence degree between the MDT's decision and the subject's decision predicted by the controlling function 131.

Moreover, in the first embodiment, in the case of displaying the list, the presenting function 132 changes the order of displaying the patients P in accordance with the degree of emergency of the treatment plan that is predicted by the controlling function 131 to have the high possibility of being chosen by the MDT from the first information; however, the present invention is not limited to this example. In another example, in a modification of the present embodiment, in the case of displaying the list, the presenting function 132 may change the order of displaying the subjects (the patients P or the people who are involved with the patients P) in accordance with the degree of emergency of the treatment plan that is predicted by the controlling function 131 to have the high possibility of being chosen by the MDT from the first information.

Moreover, in the first embodiment, the controlling function 131 predicts the patient P's decision and the MDT's decision after excluding the treatment plan that is unsuitable for the patient P among the treatment plans that the MDT may choose from the first information; however, the present invention is not limited to this example. In another example, in a modification of the present embodiment, the controlling function 131 may predict the subject's decision (the subject is the patient P or the person who is involved with the patient P) and the MDT's decision after excluding the treatment plan that is unsuitable for the subject among the treatment plans that the MDT may choose from the first information.

In addition, in the first embodiment, the storage circuitry 120 stores therein the process information expressing the procedure of the process after the controlling function 131 predicts the MDT's decision and the patient P's decision and before the MDT and the patient P agree on the treatment plan, and if the patient P's decision and the MDT's decision predicted by the controlling function 131 do not coincide, the presenting function 132 presents the recommended process that should be performed by at least one of the MDT and the patient P's doctor on the basis of process information. Here, the presenting function 132 displays the recommended process together with the information based on the result of the prediction by the controlling function 131. Moreover, upon the reception of the information expressing that the currently presented recommended process is already performed, the presenting function 132 presents the next recommended process on the basis of the process information. However, the present invention is not limited to this example. In another example, in a modification of the present embodiment, the storage circuitry 120 may store therein the process information expressing the procedure of the process after the controlling function 131 predicts the MDT's decision and the subject's decision (the subject is the patient P or the person who is involved with the patient P) and before the MDT and the subject agree on the treatment plan, and if the subject's decision and the MDT's decision predicted by the controlling function 131 do not coincide, the presenting function 132 may present the recommended process that should be performed by at least one of the MDT and the patient P's doctor on the basis of process information.

Moreover, in the second embodiment and the fourth embodiment, the controlling function 131 calculates the first probability (agreement probability) that the MDT and the patient P agree in the case where the MDT makes a decision first, and the second probability (agreement probability) that the MDT and the patient P agree in the case where the patient P makes a decision first on the basis of the preference and the acceptable range for the patient P for each of the treatment plans for the disease obtained from the first information and the preference and the acceptable range for the MDT for each of the treatment plans for the disease obtained from the second information, and the presenting function 132 determines the order of presenting the process to be performed by the MDT and the process to be performed by the patient P's doctor on the basis of the first probability and the second probability. However, the present invention is not limited to this example. In another example, in a modification of the present embodiment, the controlling function 131 may calculate the first probability (agreement probability) that the MDT and the subject (the patient P or the person who is involved with the patient P) agree in the case where the MDT makes a decision first, and the second probability (agreement probability) that the MDT and the subject agree in the case where the subject makes a decision first on the basis of the preference and the acceptable range for the subject for each of the treatment plans for the disease obtained from the first information and the preference and the acceptable range for the MDT for each of the treatment plans for the disease obtained from the second information, and the presenting function 132 may determine the order of presenting the process to be performed by the MDT and the process to be performed by the patient P's doctor on the basis of the first probability and the second probability.

Furthermore, in the third embodiment and the fourth embodiment, the controlling function 131 derives the first probability and the second probability for each number of options chosen from the treatment plans for the disease, and the presenting function 132 determines the order of presenting the number of treatment plans to be chosen by the MDT and the patient P, the process to be performed by the MDT, and the process to be performed by the patient P's doctor on the basis of the first probability and the second probability for each number of options; however, the present invention is not limited to this example. In another example, in a modification of the present embodiment, the controlling function 131 may derive the first probability and the second probability for each number of options chosen from the treatment plans for the disease, and the presenting function 132 may determine the order of presenting the number of treatment plans to be chosen by the MDT and the subject (the patient P or the person who is involved with the patient P), the process to be performed by the MDT, and the process to be performed by the patient P's doctor on the basis of the first probability and the second probability for each number of options.

Note that the components of the devices in the drawings in the present embodiment are functional, and do not necessarily need to be physically configured exactly as illustrated in the drawings. That is to say, the specific mode of the dispersion or integration of the devices is not limited to the mode illustrated in the drawings, and a part of or all of the devices may be dispersed or integrated functionally or physically in an arbitrary unit in accordance with various loads, use circumstances, and the like. In addition, each processing function performed in each device can be achieved in an arbitrary part or entirely by the CPU and the computer program analyzed and executed in the CPU, or can be achieved as the hardware by wired logic.

The method described in the present embodiment can be achieved by having a computer, such as a personal computer or a work station, execute a prepared computer program. This computer program can be distributed through a network such as the Internet. Note that this computer program may be stored in a computer-readable non-transitory storage medium such as a hard disk, a flexible disk (FD), a compact disc read only memory (CD-ROM), a magneto-optical disk (MO), or a digital versatile disc (DVD) and executed by being read out from the recording medium by the computer.

According to at least one embodiment described above, the burden on the decision making can be reduced and the reconsideration of the treatment plan can be avoided.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical treatment support apparatus, comprising: processing circuitry configured to
   predict, about a treatment plan for a disease of a patient, a decision of subjects who are the patient or people who are involved with the patient and a decision of a doctor who determines the treatment plan for the subjects; and
   present information based on a result of the prediction to the doctor and a subject of the subjects, wherein the processing circuitry is further configured to perform the prediction, based on first information about decision making performed by the subject, and second information about decision making performed by the doctor, wherein in a case of performing the prediction about a plurality of the subjects, the processing circuitry is further configured to display a list of information based on the result of the prediction for each of the subjects, wherein
   in a case of displaying the list, the processing circuitry is further configured to change an order of displaying the subjects in accordance with (1) a coincidence degree between the predicted decision of the subject and the predicted decision of the doctor, or (2) an emergency degree of the treatment plan that is predicted to have a high probability of being chosen from the first information by the doctor.

2. A medical treatment support apparatus, comprising: processing circuitry configured to
   predict, about a treatment plan for a disease of a patient, a decision of subjects who are the patient or people who are involved with the patient and a decision of a doctor who determines the treatment plan for the subjects; and
   present information based on a result of the prediction to the doctor and a subject of the subjects, wherein the processing circuitry is further configured to perform the prediction, based on first information about decision making performed by the subject, and second information about decision making performed by the doctor, wherein the processing circuitry is further configured to perform the prediction, wherein the treatment plan that is unsuitable for the subject among the treatment plans with a probability of being chosen from the first information by the doctor is excluded.

3. The medical treatment support apparatus according to claim 1, wherein the processing circuitry is further configured to additionally present the information based on the result of the prediction to another doctor, who is in charge of the patient.

4. The medical treatment support apparatus according to claim 1, further comprising storage circuitry configured to store therein process information expressing a procedure of a process after the decision of the doctor and the decision of the subject are predicted and before the doctor and the subject agree on the treatment plan, wherein
   in a case where the predicted decision of the doctor and the predicted decision of the subject do not coincide, the processing circuitry is further configured to present a recommended process to be performed by at least one of the doctor and another doctor, who is in charge of the patient, based on the process information.

5. The medical treatment support apparatus according to claim 4, wherein the processing circuitry is further configured to display the recommended process together with information based on the result of the prediction.

6. The medical treatment support apparatus according to claim 4, wherein upon reception of information expressing that the recommended process that is currently presented is already performed, the processing circuitry is further configured to present a next recommended process, based on the process information.

7. The medical treatment support apparatus according to claim 1, wherein
   the processing circuitry is further configured to derive a first probability that the doctor and the subject agree in a case where the doctor makes a decision first, and a second probability that the doctor and the subject agree in a case where the subject makes a decision first, based on a preference and an acceptable range for the subject for each of a plurality of the treatment plans for the disease obtained from the first information and a preference and an acceptable range for the doctor for each of the treatment plans for the disease obtained from the second information, and
   the processing circuitry is further configured to determine an order of presenting a process to be performed by the doctor and a process to be performed by another doctor, who is in charge of the patient, based on the first probability and the second probability.

8. The medical treatment support apparatus according to claim 7, wherein
   the processing circuitry is further configured to derive the first probability and the second probability for each number of options chosen from the treatment plans for the disease, and
   the processing circuitry is further configured to determine an order of presenting the number of treatment plans to be chosen by the doctor and the subject, the process to be performed by the doctor, and the process to be performed by the another doctor who is in charge, based on the first probability and the second probability for each number of options.

9. The medical treatment support apparatus according to claim 1, wherein the processing circuitry is further configured to present information about a coincidence degree between the predicted decision of the subject and the predicted decision of the doctor.

10. The medical treatment support apparatus according to claim 1, wherein
    the processing circuitry is further configured to derive an agreement probability that the doctor and the subject agree on each of a plurality of the treatment plans for the disease, based on a preference of the subject for each of the treatment plans for the disease obtained from the first information and a preference of the doctor for each of the treatment plans for the disease obtained from the second information, and the processing circuitry is further configured to present information according to a value of the agreement probability that is derived.

11. The medical treatment support apparatus according to claim 2, wherein the processing circuitry is further configured to present information about a coincidence degree between the predicted decision of the subject and the predicted decision of the doctor.

12. The medical treatment support apparatus according to claim 2, wherein the processing circuitry is further configured to derive an agreement probability that the doctor and the subject agree on each of a plurality of the treatment plans for the disease, based on a preference of the subject for each of the treatment plans for the disease obtained from the first information and a preference of the doctor for each of the treatment plans for the disease obtained from the second information, and the processing circuitry is further configured to present information according to a value of the agreement probability that is derived.

13. The medical treatment support apparatus according to claim 2, wherein the processing circuitry is further configured to additionally present the information based on the result of the prediction to another doctor, who is in charge of the patient.

14. The medical treatment support apparatus according to claim 2, further comprising storage circuitry configured to store therein process information expressing a procedure of a process after the decision of the doctor and the decision of the subject are predicted and before the doctor and the subject agree on the treatment plan, wherein in a case where the predicted decision of the doctor and the predicted decision of the subject do not coincide, the processing circuitry is further configured to present a recommended process to be performed by at least one of the doctor and another doctor, who is in charge of the patient, based on the process information.

15. The medical treatment support apparatus according to claim 2, wherein the processing circuitry is further configured to derive a first probability that the doctor and the subject agree in a case where the doctor makes a decision first, and a second probability that the doctor and the subject agree in a case where the subject makes a decision first, based on a preference and an acceptable range for the subject for each of a plurality of the treatment plans for the disease obtained from the first information and a preference and an acceptable range for the doctor for each of the treatment plans for the disease obtained from the second information, and the processing circuitry is further configured to determine an order of presenting a process to be performed by the doctor and a process to be performed by another doctor, who is in charge of the patient, based on the first probability and the second probability.

* * * * *